(12) United States Patent  
Rafaat

(10) Patent No.: US 9,302,052 B1  
(45) Date of Patent: Apr. 5, 2016

(54) PRE-LOADED SYRINGE WITH METERED DOSING AND METHODS OF USE

(71) Applicant: Karim Timothy Rafaat, La Jolla, CA (US)

(72) Inventor: Karim Timothy Rafaat, La Jolla, CA (US)

( * ) Notice: Subject to any disclaimer, the term of this patent is extended or adjusted under 35 U.S.C. 154(b) by 313 days.

(21) Appl. No.: 13/874,256

(22) Filed: Apr. 30, 2013

(51) Int. Cl.  
*A61M 5/315* (2006.01)

(52) U.S. Cl.  
CPC ................. *A61M 5/31578* (2013.01)

(58) Field of Classification Search  
CPC .......... A61M 5/31548; A61M 5/3156; A61M 5/31555; A61M 5/31595; A61M 5/31563; A61M 5/31591  
See application file for complete search history.

(56) References Cited

U.S. PATENT DOCUMENTS

| | | | |
|---|---|---|---|
| 7,470,259 B2 * | 12/2008 | Hoyle, Jr. .................. | 604/207 |
| 2004/0162528 A1 * | 8/2004 | Horvath et al. ............ | 604/207 |
| 2008/0108952 A1 * | 5/2008 | Horvath et al. ............ | 604/208 |
| 2014/0303565 A1 * | 10/2014 | Kubo et al. ................ | 604/208 |

FOREIGN PATENT DOCUMENTS

WO  WO 2012118687  * 9/2012 ............. A61M 5/32

* cited by examiner

*Primary Examiner* — Aarti B Berdichevsky  
(74) *Attorney, Agent, or Firm* — Sheppard Mullin Richter & Hampton LLP

(57) ABSTRACT

Methods and devices for metering and delivering a desired dose of medication from a syringe are described. The devices comprise dosage limiting sleeve adjustably disposed around a syringe body, wherein the alignment of the dosage limiting sleeve relative to the syringe body indicates the dose to be administered by depressing a plunger until the dosage limiting sleeve is engaged.

9 Claims, 4 Drawing Sheets

PRE-LOADED SYRINGE WITH METERED DOSING AND METHODS OF USE

TECHNICAL FIELD

The present disclosure is generally related to liquid medication delivery devices and their methods of use. In particular, the present disclosure provides a syringe body with an adjustable plunger stop to meter a single dose to be delivered.

BACKGROUND OF THE INVENTION

In a hurried and pressure-ridden work environment, such as a surgical operating room, there is always a risk for errors to occur. Medication errors may be particularly at risk in the event of an emergency administration of an injectable drug, e.g., while a patient is coding. This is because performing the appropriate calculations to account for drug concentration and volume to be administered based on patient physical characteristics can be difficult under heightened stress conditions. In fact, the steps involved in drug dose calculation, preparation, and administration are constantly identified as steps in pediatric resuscitation that are prone to error, and may be associated with significant morbidity and/or mortality in emergency situations.

Moreover, medication errors related to emergency administration of an injectable medication are not limited to surgical operating rooms. Health care arenas where emergency administrations (to adults, children, or both) occur infrequently are typically staffed by personnel who are less than ideally familiar with calculation, preparation, and administration of injectable medications under emergency conditions.

SUMMARY OF THE INVENTION

In one aspect, pre-loaded syringes are described that include: a syringe body for storing and dispensing a liquid contained within the syringe body; a plunger arranged partially within the syringe body such that translational motion of the plunger in a proximal direction causes the liquid to be dispensed from the syringe body; a housing attached to and disposed around at least a portion of the syringe body in such a way as to define a gap between the housing and the syringe body, the gap extending at least a portion of the length of the syringe body, wherein the gap is open at a distal end of the syringe body; and a dosage limiting sleeve adjustably disposed within the gap and extending in a distal direction beyond the distal end of the syringe body and housing; wherein a distal end of the dosage limiting sleeve is configured to interact with a proximal surface of a distal end of the plunger so as to prevent translational motion of the plunger in a proximal direction beyond a predetermined point, but the dosage limiting sleeve does not limit translational motion of the plunger in a distal direction.

In some embodiments, an exterior surface of the syringe body and an interior surface of the housing define concentric cylinders.

In some embodiments, at least one of an inner surface or outer surface of the dosage limiting sleeve and at least one of an inner surface of the housing or an outer surface of the syringe body are threaded. In some related embodiments, the limit of translational motion of the plunger in a proximal direction is set by rotating the dosage limiting sleeve relative to the housing and syringe body.

In some embodiments, the portion of the dosage limiting sleeve that extends beyond the distal end of the syringe body further includes one or more outwardly directed protuberances, wings, tabs, or other grip enhancing surface modifications.

In some embodiments, at least a portion of the syringe body and housing are colorless and transparent so as to allow a user to see at least a portion of the liquid contents of the syringe body.

In some embodiments, the dosage limiting sleeve is made of a colored material. In some related embodiments, the colored material is a transparent colored material. In some related embodiments, the color of the dosage limiting sleeve is an indication as to the category or identity of the liquid contents of the syringe body.

In some embodiments, the syringe body or housing include a plurality of non-volumetric graduations viewable by a user for measuring the dosage to be dispensed. In some related embodiments, the non-volumetric graduations are keyed to the identity and concentration of the contents of the pre-loaded syringe such that the graduations indicate the appropriate dosage of the particular liquid in the pre-loaded syringe by patient weight. In some embodiments, the non-volumetric graduations are printed on or etched into the syringe body or housing. In alternate embodiments, the non-volumetric graduations may be separately printed on a label that is attached to the housing at the appropriate location during or after manufacture of the device.

In some embodiments, the dosage limiting sleeve includes a plurality of graduations for measuring the dosage to be dispensed. In some related embodiments, the plurality of graduations is a plurality of non-volumetric graduations. In some further related embodiments, the non-volumetric graduations are keyed to the identity and concentration of the contents of the pre-loaded syringe such that the graduations indicate an appropriate dosage of the particular liquid in the pre-loaded syringe by patient weight. In some embodiments, the non-volumetric graduations are printed on or etched into the dosage limiting sleeve. In alternate embodiments, the non-volumetric graduations may be separately printed on a label that is attached to the dosage limiting sleeve at the appropriate location during or after manufacture of the device.

In another aspect, methods of administering a liquid medication to a patient with a pre-loaded syringe including a syringe body fbr storing and dispensing a liquid contained within the syringe body, and a plunger arranged at least partially within the syringe body such that translational motion of the plunger in a proximal direction causes the liquid to be dispensed from the syringe body are presented. In these methods, a plurality of non-volumetric graduations are keyed to the identity and concentration of the contents of the pre-loaded syringe such that the graduations indicating an appropriate dose of the liquid in the pre-loaded syringe by patient weight is present on the pre-loaded syringe and viewable by a user. The methods include moving the plunger in a proximal direction within the syringe body until a proximal end of the plunger aligns with a desired non-volumetric graduation.

In some embodiments, the pre-loaded syringe further includes an adjustable dose limiter that is configured to interact with a proximal surface of a distal end of the plunger so as to prevent translational motion of the plunger in a proximal direction beyond a predetermined point without limiting translational motion of the piston in a distal direction. In some related embodiments, the adjustable dose limiter is a dose limiting sleeve configured to surround at least a portion of the syringe body. In some further related embodiments, the length of the adjustable dose limiting sleeve and location of the plurality of non-volumetric graduations is such that a proximal end of the dose limiting sleeve aligns with the non-volumetric graduations so as to indicate the dose to be delivered when the plunger is moved in a proximal direction to the fullest extent allowed by the dose limiting sleeve. In these embodiments, the methods include a first step of adjusting the dose limiting sleeve such that a proximal end of the dosage limiting sleeve is aligned with a desired non-volumetric graduation.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1:
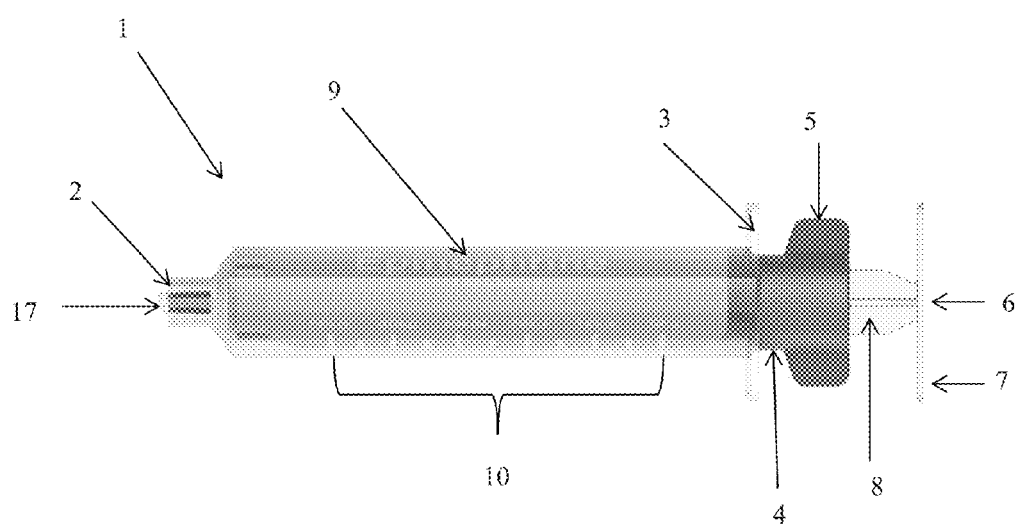
FIG. 1 is a side view of an exemplary syringe according to one embodiment.

The drawings are described in greater detail in the description and examples below.

DETAILED DESCRIPTION

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

The present disclosure relates in general to apparatus and methods for increasing the safety of administration of a liquid medication, particularly under emergency conditions. Various embodiments of the present invention provide drug delivery devices, such as syringes, and methods of enabling users to administer an appropriate dose of a medication from such devices while reducing the risk for error in determining and/or administering an appropriate dose of the medication, thus reducing the risk of patient harm.

Every health-care practitioner should expect to be involved in the treatment of medical emergencies during the course of clinical practice. Certain medical emergencies require the administration of an injectable medication for a favorable patient outcome. Under what may be very infrequently encountered conditions, a health-care practitioner may be required to assess a medical emergency, identify and access an appropriate medication, determine an appropriate amount to administer, and effectively administer a correct dosage, all while a patient is experiencing a life-threatening medical emergency. Under such conditions, mistakes can occur particularly as it is unlikely that a medical practitioner deals with such situations on a routine basis.

It has been recognized that certain steps may be taken to help mitigate risks involved in treatment of medical emergencies. For instance, the most commonly needed emergency medications are typically on hand and readily available at all medical treatment facilities, including but not limited to emergency rooms, operating rooms, clinics, emergency response vehicles, even dental care facilities.

Certain embodiments of the present invention are designed to reduce or eliminate some of the potential sources of error faced by a user administering an injectable medication in a medical emergency.

In some embodiments an emergency injectable medication is provided pre-loaded in a syringe. These pre-loaded syringes may be color coded so as to indicate the category, if not the specific identity, of the medication contained therein. By way of example, pre-loaded syringes may be color coded according to conventional operating room protocols (i.e., purple for epinephrine, ephedrine, neosynephrine; green for atropine and glycopyrollate; blue for opioids; orange for benzodiazepenes; white for electrolyte solutions; etc.). However, it is to be understood that use of a color coding system does not typically replace traditional syringe labeling, e.g., labeling with the identity and concentration of the contents of the syringe. Further, use of a color coding system should not interfere with or prevent a user from viewing any identifying labeling that may be present on the pre-loaded syringe or prevent a user from measuring a dose for administration.

In some embodiments, syringes are provided that are labeled with non-volumetric graduations keyed to the identity and concentration of the contents of the pre-loaded syringe, such as graduations based on the weight of the patient. Such syringes have the advantage that a user is not required to recall the particular drug's dosage rate/kg, thus eliminating accurate recall of this detail as a potential source of error. Further, a user is not required to do a calculation to determine the appropriate volume of the keyed drug to administer. Instead, a user would merely select an amount to administer based on the weight of a patient.

In some embodiments where the syringe is not pre-loaded (i.e., the user is required to draw an appropriate dose of a medication into the syringe prior to administration), the non-volumetric graduations may start at zero at the limit of plunger travel at the proximal end of the syringe (i.e., the end at which medication is dispensed) and go upwards to a maximum near the distal end of the syringe. Thus, a user would draw a dose for a particular patient into the syringe by drawing the syringe to the appropriate graduation for the particular patient. The entire volume then contained in the syringe would be the appropriate dose for the particular patient.

In some embodiments where the syringe is pre-loaded, non-volumetric graduations may start at zero at the pre-filled level near the distal end of the syringe and progress to a maximum at the limit of plunger travel at the proximal end of the syringe. In these embodiments, an appropriate dose for a particular patient is achieved by administering drug from the syringe until the proximal end of the plunger aligns with the graduation corresponding to the non-volumetric graduation appropriate for the particular patient.

In some embodiments, pre-loaded syringes are provided that comprise an adjustable means to limit plunger travel in a proximal direction, thus limiting the amount of drug that can be administered from the pre-loaded syringe to some amount less than the total amount of drug contained within the pre-loaded syringe. That is, pre-loaded syringes are provided that allow a user to limit the amount of medication administered from the syringe by preventing plunger travel in a proximal direction beyond a set distance. In some embodiments, plunger travel is limited in a proximal direction, but not in a distal direction.

Figure 2:
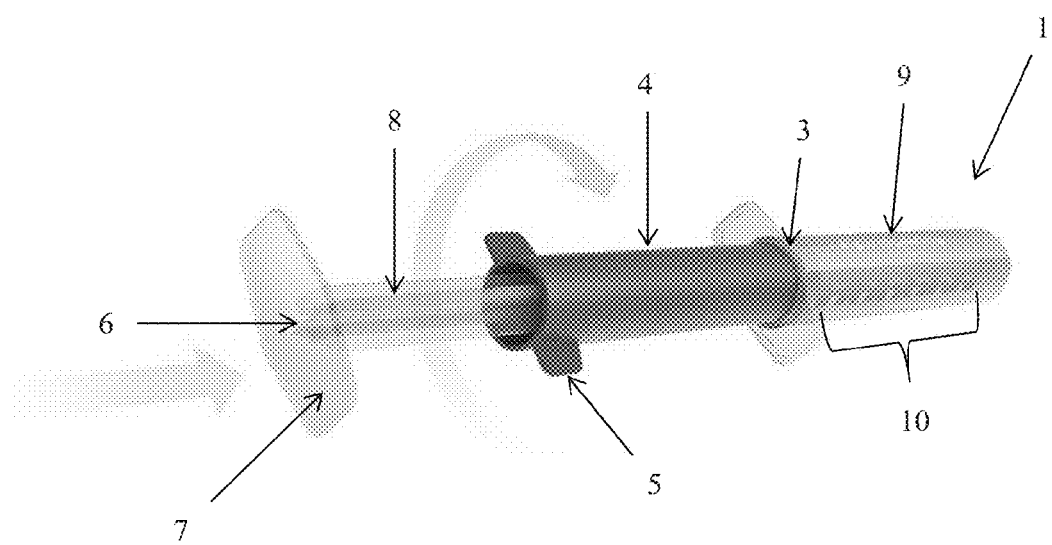
FIG. 2 is an off-axis view from the distal end of an exemplary syringe according to one embodiment.
Figure 3:
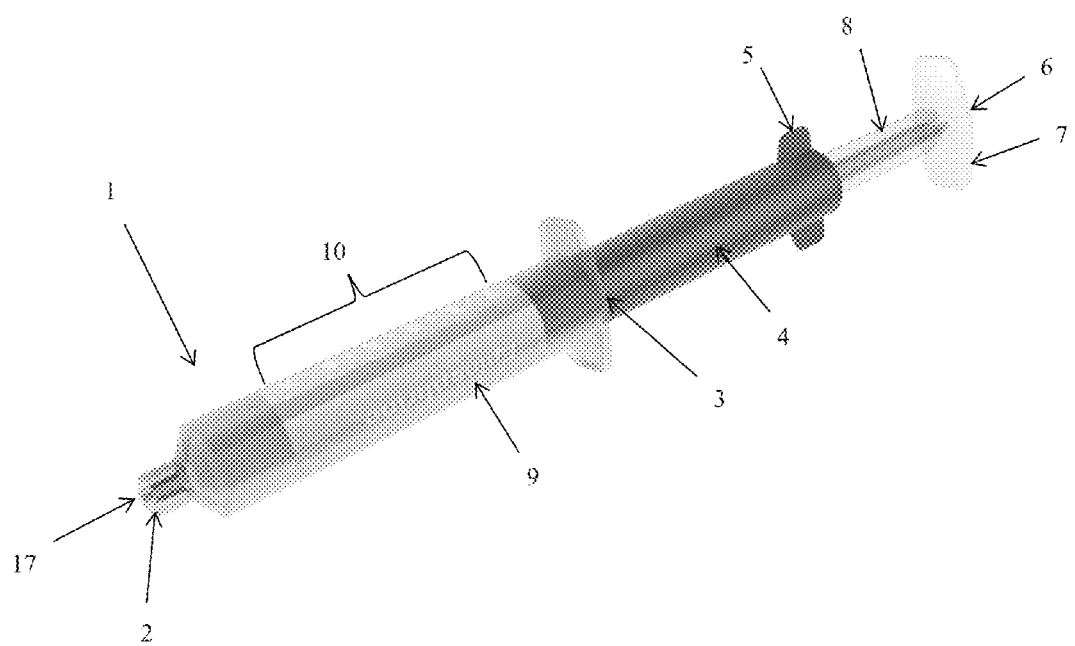
FIG. 3 is an off-axis view from the proximal end of an exemplary syringe according to one embodiment.
Figure 4:
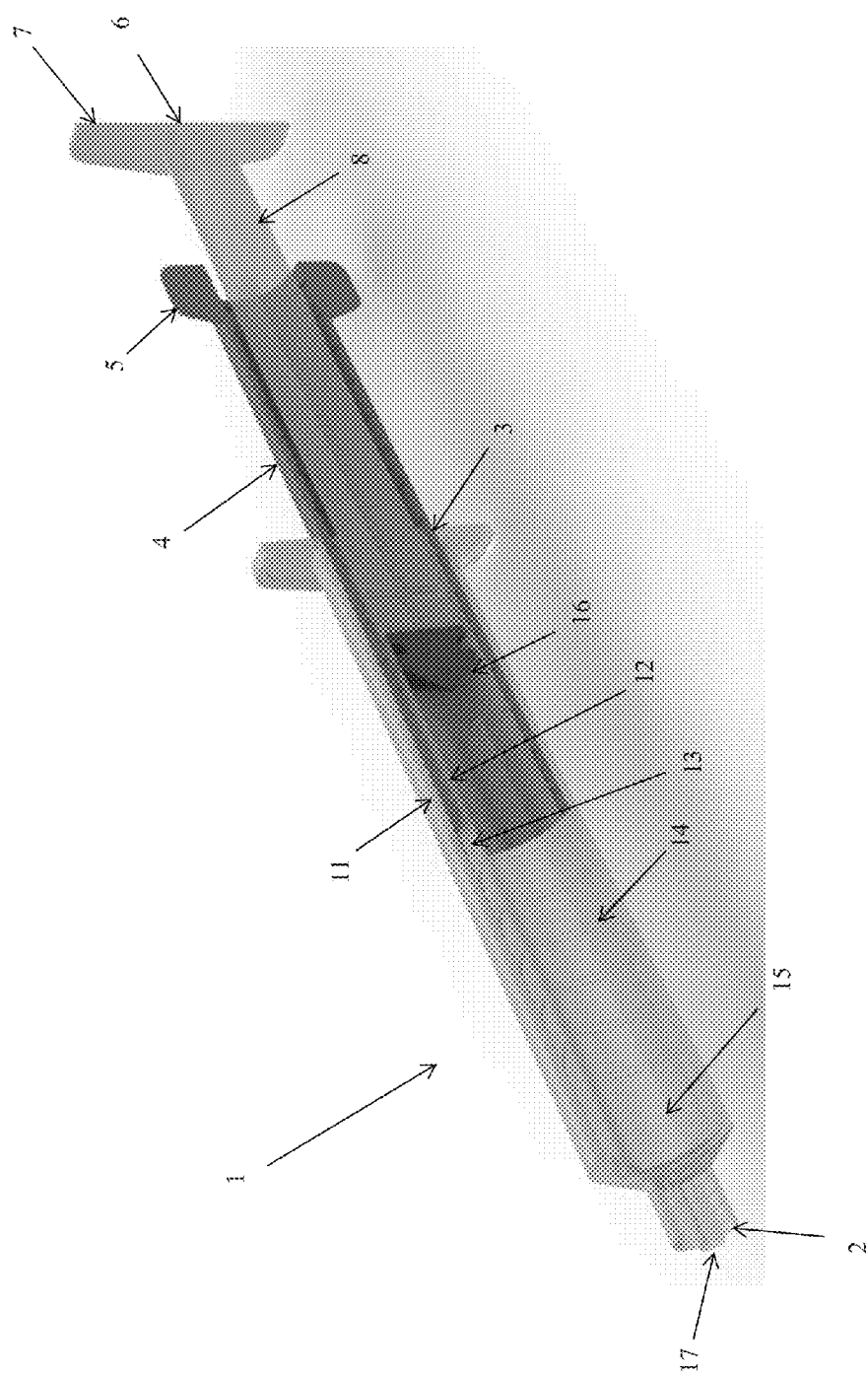
FIG. 4 is a cross-sectional view of an exemplary syringe according to one embodiment.

An exemplary pre-loaded syringe will be discussed with reference to FIGS. 1-4. An exemplary embodiment 1 for storing and dispensing a liquid has a proximal end 2 and a distal end 3. The exemplary embodiment comprises a syringe body 12 defining a void space 15 where a liquid is contained and dispensed therefrom. The syringe body 12 is attached to and at least partially surrounded by a housing 11. The housing 11 is attached to and disposed around the syringe body 12 in such a way so as to define a gap 13 between the housing 11 and the syringe body 12 that extends at least a portion of the length of the syringe body 12.

A dosage limiting sleeve 4 is adjustably disposed within gap 13 and contacts one or more of an outer surface of syringe body 12, an inner surface of housing 11, or both. The depth of the dosage limiting sleeve 4 within gap 13 serves to set the maximum distance a plunger 6 can travel in a proximal direction, thereby setting a maximum dosage to be administered. As the dose limiting sleeve is disposed in gap 13 between the housing 11 and the syringe body 12, the instant devices may be constructed such that no portion of the dose limiting sleeve 4 enters a void 15 defined by the syringe body 12.

Adjustability of the dosage limiting sleeve 4 may be accomplished by any suitable means as will be appreciated by one in the art. In some embodiments, an inner surface of the dosage limiting sleeve 4 and an outer surface of the syringe body 12 (i.e., a surface facing gap 13 and contacting an inner surface of dosage limiting sleeve 4) may be threaded so as to provide depth adjustment of the dosage limiting sleeve 4 within gap 13 by rotating the dosage limiting sleeve 4 relative to syringe body 12. Such an embodiment is seen in the cross-sectional view shown in FIG. 4, where threads 14 are seen disposed on an outer surface of the syringe body 12. The corresponding threads on the dosage limiting sleeve 4 are not shown.

Alternatively or in addition, an outer surface of the dosage limiting sleeve 4 and an inner surface of the housing 11 (i.e., a surface facing gap 13 and contacting an outer surface of dosage limiting sleeve 4) may be threaded so as to provide depth adjustment of dosage limiting sleeve 4 within gap 13 by rotating the dosage limiting sleeve relative to housing 11.

As seen in the Figures, some portion of the dosage limiting sleeve 4 extends in a distal direction beyond the syringe body 12 and housing 11I. This portion may comprise protuberances, wings, tabs, or other grip enhancing features (such as surface patterns) that facilitate adjustment of the depth of the dosage limiting sleeve 4 within gap 13. In the exemplary embodiment shown in the Figures, the dosage limiting sleeve 4 is shown with optional tabs 5 for this purpose.

Housing 11 and syringe body 12 may be made of any suitable material so long as a portion of the housing 11 and syringe body 12 allow a user to view the liquid contained therein. In particular embodiments, housing 11 and syringe body 12 may comprise a clear, colorless material, such as an appropriate plastic, to allow a user to clearly view the contents of the syringe. The dosage limiting sleeve 4 may also be made of any suitable material, including a suitable plastic. Further, at least a portion of the dosage limiting sleeve 4 viewable by a user may be color coded to correspond with the category and/or identity of the specific medication contained within a syringe. One embodiment that includes this optional feature is seen in the Figures, in which the entire dosage limiting sleeve 4 is colored. However, in other embodiments, other color coding schemes may be employed, such as color coding only a portion of the dosage limiting sleeve 4, color coding all or a portion of a plunger (described below), etc. In fact, any portion of the device may be color coded so long as the color coding does not prevent a user from viewing any identifying labeling on the device, or prevent a user from metering a dose.

Also, as described above, the instant devices may be labeled with non-volumetric graduations, such as graduations based on the weight of the patient. This optional feature is seen as element 10 in the exemplary embodiment shown in the Figures.

Additionally, the instant devices may be labeled with other information identifying the specific identity and concentration of the medication contained within. This optional feature is particularly relevant for pre-loaded syringe devices, and is seen as element 9 in the exemplary embodiment shown in the Figures.

The instant devices also comprise a typical plunger 6 as previously known in the art. The plunger 6 comprises a piston rod 8 disposed at least partially within the syringe body 12. The plunger 6 further comprises a gasket 16 disposed at a proximal end of the piston rod 8 and a thumb pad 7 at a distal end of the piston rod 8. The gasket 16 is constructed of an appropriate material and is of an appropriate shape and size so as to form a seal by contacting the interior surface of the syringe body 12. In some embodiments, the gasket 16 and the piston rod 8 do not contact the dose limiting sleeve 4 at any point before, during, or after administration.

A plunger 6 also comprises a thumb pad 7, which in general is not intended to be limited in size and/or shape. However, in embodiments comprising a dose limiting sleeve 4, the thumb pad 7 has at least one dimension that exceeds an interior dimension of the dose limiting sleeve 4.

The operation of plunger 6 within a syringe body will be familiar to one of skill in the art, with the plunger 6 partially disposed within the syringe body 11 such that translational motion of the plunger 6 through the syringe body 11 in a proximal direction causes the contents of the syringe body to be ejected from the syringe body 11 at an opening 17.

In some embodiments, the lengths of the plunger 6 and the dose limiting sleeve 4 are such that when the plunger 6 is fully depressed and a proximal surface of the thumb pad 7 is in contact with the distal end of the dosage limiting sleeve 4, a proximal end of the plunger 6 aligns with a proximal end of the dosage limiting sleeve 4.

In some embodiments, devices described herein may further comprise a hypodermic needle of appropriate length and diameter for an intended injectable medication. In some embodiments, a device may be constructed with a hypodermic needle integral to and/or permanently affixed to a proximal end 2 of the device. Alternatively, the device may be constructed such that a proximal end 2 may be configured to releasable receive a hypodermic needle by any suitable means known in the art, such as screw threading or a Luer lock.

Thus, the exemplary pre-loaded syringe shown in the Figures may be used as follows. A user assesses or obtains the weight of a patient in need of administration of an injectable medication contained within the exemplary pre-loaded syringe device. The user adjusts the depth of the dose limiter sleeve 4 so that a proximal end of the sleeve 4 aligns with a graduation indicating a desired dose. Using the particular embodiment shown in the Figures, this means that a user adjusts the depth of the dose limiter sleeve 4 so that the proximal end of sleeve 4 aligns with an appropriate weight graduation 10 corresponding to the weight of the patient. The user administers the liquid contained in the syringe by depressing the thumb pad 7, thereby moving the plunger 6 in a proximal direction and expelling the liquid through opening 17, until a proximal surface of the thumb pad 7 contacts a distal end of the dose limiter sleeve 4. Once the thumb pad 7 contacts a distal end of the dose limiter sleeve 4, the desired dose has been delivered and plunger 6 is prevented from further travel.

As will be appreciated by those of skill in the art, use of the instant devices is not intended to be limited to any particular medication. Rather, any appropriate medication may be stored in and/or dispensed from the instant devices, so long as the medication may be stored in and/or dispensed from a syringe type device. In some particular embodiments, a medication may be selected from the group consisting of an inotrope (such as epinephrine, ephedrine, neosynephrine, etc.), an anticonvulsant, an analgesic, a vasopressor, an antihypoglycemic, a corticosteroid, an antihypertensive, an anticholinergic, an antiarrhythmic, a vasodilator, and an antidotal.

It is also not intended that the instant devices are limited with respect to volumetric capacity. Instant devices may be constructed to hold any necessary volume of an intended medication. Additionally, although the exemplary devices shown in the Figures comprise concentric cylindrical syringe bodies and housings, the cross-sectional shapes of the housing and syringe body are not necessarily limited as such. Any desired cross-sectional shape of the syringe body, housing, or both may be used, so long as a gap is defined between the housing and syringe body within which the dose limiting sleeve is adjustably disposed.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

What is claimed is:

1. A pre-loaded syringe comprising:
    a syringe body for storing and dispensing a liquid contained within the syringe body;
    a plunger arranged partially within the syringe body such that translational motion of the plunger in a proximal direction causes the liquid to be dispensed from the syringe body;
    a housing attached to and disposed around at least a portion of the syringe body in such a way as to define a gap between the housing and the syringe body, the gap extending at least a portion of a length of the syringe body, wherein the gap is open at a distal end of the syringe body; and
    a dosage limiting sleeve adjustably disposed within the gap and extending in a distal direction beyond the distal end of the syringe body and housing; wherein a distal end of the dosage limiting sleeve is configured to interact with a proximal surface of a distal end of the plunger so as to prevent translational motion of the plunger in a proximal direction beyond a predetermined point, and wherein the dosage limiting sleeve does not limit translational motion of the piston in a distal direction, wherein one of the syringe body, the housing, or the dosage limiting sleeve comprises non-volumetric graduations keyed to an identity and concentration of the liquid such that the graduations indicate an appropriate dosage of the liquid by patient weight.

2. The pre-loaded syringe of claim 1, wherein an exterior surface of the syringe body and an interior surface of the housing define concentric cylinders.

3. The pre-loaded syringe of claim 1, wherein the portion of the dosage limiting sleeve that extends beyond the distal end of the syringe body further comprises one or more outwardly directed protuberances, wings, tabs, or other grip enhancing surface modifications.

4. The pre-loaded syringe of claim 1, wherein the syringe body and housing are colorless and transparent.

5. The pre-loaded syringe of claim 1, wherein the non-volumetric graduations are viewable by a user for measuring the dosage to be dispensed.

6. The pre-loaded syringe of claim 1, wherein at least one of an inner surface or outer surface of the dosage limiting sleeve and at least one of an inner surface of the housing or an outer surface of the syringe body are threaded.

7. The pre-loaded syringe of claim 6, wherein the limit of translational motion of the plunger in a proximal direction is set by rotating the dosage limiting sleeve relative to the housing and syringe body.

8. The pre-loaded syringe of claim 1, wherein the dosage limiting sleeve is made of a colored material.

9. The pre-loaded syringe of claim 8, wherein the color of the dosage limiting sleeve is an indication as to the category or identity of the liquid of the syringe body.

* * * * *